(12) United States Patent
Wolowelsky et al.

(10) Patent No.: US 9,880,094 B2
(45) Date of Patent: Jan. 30, 2018

(54) INFRARED DETECTION AND IMAGING DEVICE WITH NO MOVING PARTS

(71) Applicants: CI SYSTEMS ISRAEL LTD., Migdal Haemek (IL); TECHNION RESEARCH & DEVELOPMENT FOUNDATION LIMITED, Haifa (IL)

(72) Inventors: Karni Wolowelsky, Eshhar (IL); Carmel Rotschild, Ganey Tikva (IL); Dario Cabib, Timrat (IL); Amir Gil, Kiryat Tivon (IL)

(73) Assignees: CI SYSTEMS ISRAEL LTD, Migdal Haemek (IL); TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 15/442,715

(22) Filed: Feb. 27, 2017

(65) Prior Publication Data
US 2017/0167972 A1 Jun. 15, 2017

Related U.S. Application Data

(63) Continuation of application No. 14/936,704, filed on Nov. 10, 2015, now Pat. No. 9,581,543.
(Continued)

(51) Int. Cl.
*G01N 21/3504* (2014.01)
*G01N 21/31* (2006.01)
(Continued)

(52) U.S. Cl.
CPC ....... *G01N 21/3504* (2013.01); *G01N 21/314* (2013.01); *G02F 1/137* (2013.01);
(Continued)

(58) Field of Classification Search
CPC ... G01N 21/3504; G01N 21/314; G02F 1/137
See application file for complete search history.

(56) References Cited

U.S. PATENT DOCUMENTS 3,711,181 A 1/1973 Adams, Jr. et al.
4,099,854 A 7/1978 Decker et al.
(Continued)

FOREIGN PATENT DOCUMENTS

CN 201666992 U 12/2010

*Primary Examiner* — David Porta
*Assistant Examiner* — Mindy Vu
(74) *Attorney, Agent, or Firm* — Mark M. Friedman

(57) ABSTRACT

A device images radiation from a scene. A detector is sensitive to the radiation in a first wavelength band. A lens forms an image of the scene on the detector. A filtering arrangement includes two sets of radiation absorbing molecules. A control unit switches the filtering arrangement between two states. In the first state, all of the radiation in the first wavelength band is transmitted to the detector. In the second state, the radiation in a second wavelength band within the first wavelength band is absorbed by the radiation absorbing molecules. The control unit synchronizes the switching of the filtering arrangement with the detector. Each pixel of the image formed on the detector includes two signals. The first signal includes information from the scene radiation in the first wavelength hand. The second signal excludes information from the scene radiation absorbed by the filtering arrangement in the second wavelength band.

5 Claims, 7 Drawing Sheets

Related U.S. Application Data

(60) Provisional application No. 62/077,328, filed on Nov. 10, 2014.

(51) Int. Cl.
  *G02F 1/137* (2006.01)
  *H04N 5/33* (2006.01)

(52) U.S. Cl.
  CPC ............ *G01N 2021/317* (2013.01); *G01N 2021/3531* (2013.01); *H04N 5/33* (2013.01)

(56) References Cited

U.S. PATENT DOCUMENTS

| | | | |
|---|---|---|---|
| 5,612,738 A | 3/1997 | Kim | |
| 8,653,461 B1 | 2/2014 | Benson | |
| 2007/0070260 A1 | 3/2007 | Wang | |
| 2007/0195227 A1* | 8/2007 | Dufresne | G02F 1/1337 349/96 |
| 2007/0241280 A1 | 10/2007 | Dainobu et al. | |
| 2007/0247709 A1 | 10/2007 | Karakawa | |
| 2010/0284570 A1* | 11/2010 | Grimberg | G01M 3/002 382/103 |
| 2010/0315567 A1* | 12/2010 | Wen | G01J 4/04 349/18 |
| 2012/0145906 A1 | 6/2012 | Treado et al. | |
| 2013/0188074 A1* | 7/2013 | Nakabayashi | H04N 5/238 348/223.1 |
| 2014/0002667 A1 | 1/2014 | Cheben | |
| 2014/0098309 A1 | 4/2014 | Shi et al. | |
| 2014/0168546 A1* | 6/2014 | Magnusson | A41D 13/1184 349/14 |
| 2015/0332081 A1 | 11/2015 | LaForest et al. | |
| 2016/0131576 A1 | 5/2016 | Cabib et al. | |

* cited by examiner

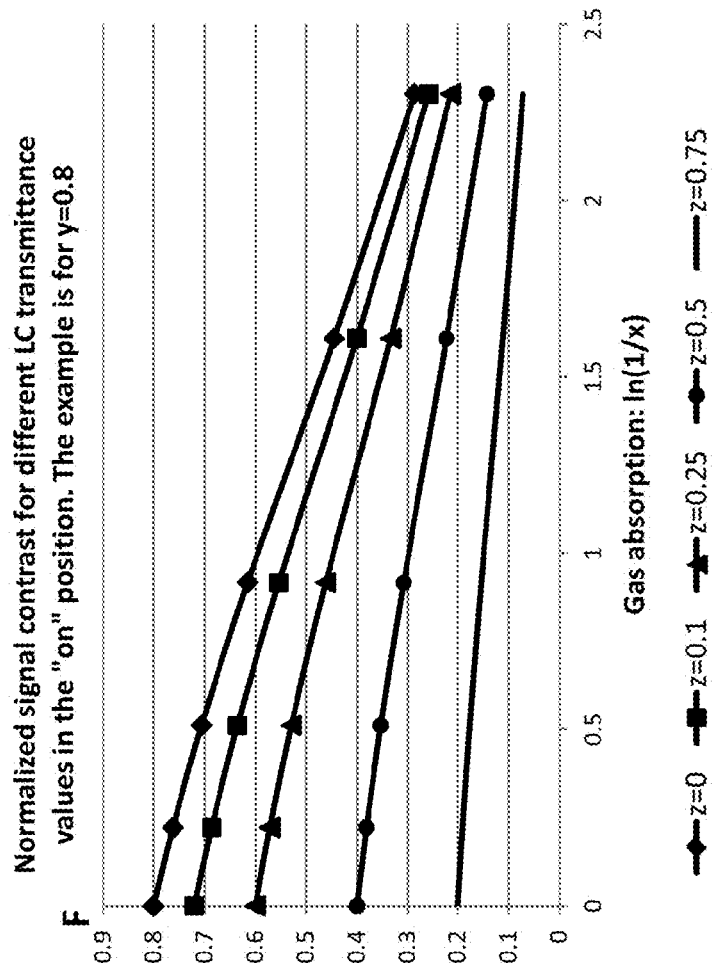
FIG. 4
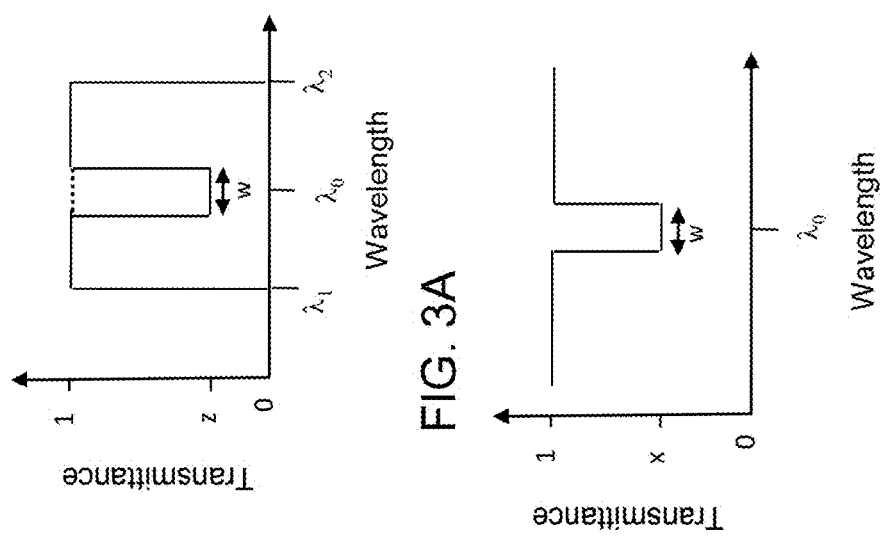
FIG. 3A
FIG. 3B

FIGURE 5 IR transmission of a 15-μm, parallel-aligned E-7 LC mixture. The truncation at the ~40-μm region is due to the KRS-5 substrates used.

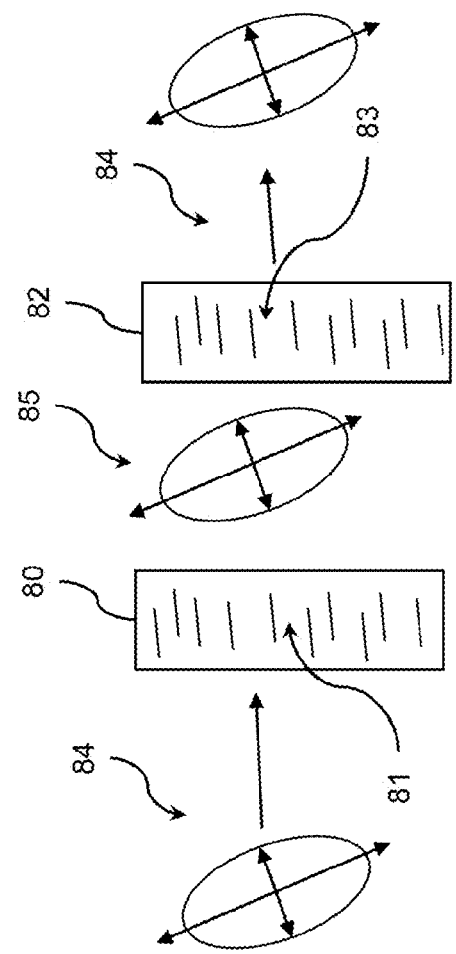
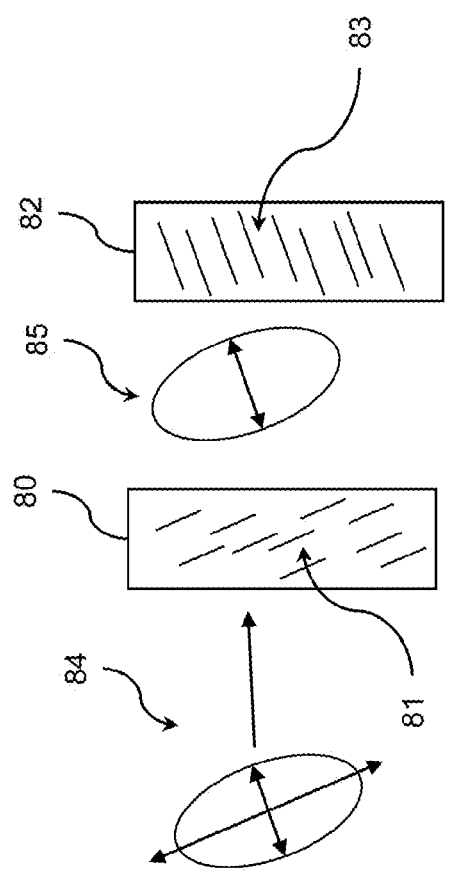
FIG. 8A
FIG. 8B

INFRARED DETECTION AND IMAGING DEVICE WITH NO MOVING PARTS

CROSS-REFERENCE TO RELATED APPLICATIONS

This application claims priority from U.S. Provisional Patent Application No. 62/077,328, filed Nov. 10, 2014, whose disclosure is incorporated herein by reference.

TECHNICAL FIELD

The present invention relates to the detection and imaging of infrared radiation.

BACKGROUND OF THE INVENTION

The last twenty five years have seen a very large amount of work done in the field of multispectral and spectral imaging all around the world, in industry and academia. The motivation is to collect spatially and spectrally resolved radiance information of a predefined region of space. The number and fields of application of such information are innumerable; as a result, the different optical configurations used in the design of instrumentation built for this purpose have also been innumerable, in order to provide the needed information through a method and format most suitable for the relevant application. Instrumentation has been built for laboratory and field use, industrial and military use, on land, on the sea, from the air and in space. Such types of instrumentation are based in the visible spectral range (400-750 nanometers), and in the various regions of infrared (the Near Infrared (NIR) range of 750-2500 nanometers, the Mid Wave Infrared (MWIR) range of 2500-5000 nanometers, and the Long Wave Infrared (LWIR) of 5000-14000). Instrumentation of spectral imaging has been built for analysis of microscopic samples in hospital environments, as well as of distant cosmic objects through large astronomical telescopes. The size of the analyzed region of space and spatial resolution also vary widely, as well as the spectral resolution, depending on the type of detector used (i.e. the size, speed, sensitivity and number of resolution elements (pixels) that the detector provides). All work done in this field allows the acquisition of knowledge of the spatial distribution (the imaging side) of the material constituents (the spectroscopic side) in a predefined region of space. Just one of many examples of early commercial spectral imagers is the microscope mounted SpectraCube 1000 of the early nineties ("Novel spectral imaging system combining spectroscopy with imaging applications for biology", Proc. SPIE Vol. 2329, 180 (1995), and U.S. Pat. No. 5,539,517), sensitive in the visible range, invented at CI Systems in 1991 and transferred to Numetrix and later to Applied Spectral Imaging Ltd. for use in medical applications.

The early drive in the 1990's was to make the transition from systems based on imaging at a limited number of wavelengths using bandpass filters (below ten) used on satellites (like Landsat and similar instruments of the 1970's and 1980's), to hyperspectral imaging, providing hundreds of spectral resolution elements at each image pixel, using gratings and interferometers and sophisticated optics. The latter group, especially through advances in modern cooled or chilled CCD's and cryogenically cooled infrared detector arrays, represents a high end type of instrumentation. Such high end instrumentation provides large quantities of information, but is usually more suitable for research projects and not for practical day-to-day civilian and industrial applications, due to exceedingly high costs which may reach hundreds of thousands of dollars each.

A more recent trend is to exploit spectral imaging technology for safety, security and industrial applications, and in particular in the application of hazardous gas cloud detection and imaging. Spectral imaging technology as applied to such applications can be used, for example, in automatic detection of leaks in industrial installations without the need for manpower intensive maintenance investigations, and to identify gases liberated to the air in traffic accidents involving trucks during transport. The low price and maintenance-free operation required for this type of instrumentation is a strong motivation to use low price detectors with no moving parts. Both are significant challenges: i) the former, because most hazardous gases in safety applications are transparent in the visible range and require more expensive infrared detectors, in order to be detected; ii) the latter, because the need for simultaneous spatial and spectroscopic information needed for detection and identification is more easily achieved with a spectral scanning method of some kind, usually requiring the movement of some optical component, such as a scanning mirror of an interferometer, a set of band pass filters mounted on a rotating wheel, or other.

Recent technological advances have allowed the development of more cost effective infrared detectors and cameras not requiring cooling at all, or at most requiring thermoelectric cooling (for example microbolometers MIR detectors and MWIR PbSe arrays). As a result, the motivation to find optical configurations yielding just the right amount of information for a specific application, while maintaining low cost, has also become very strong. Compromises in this respect have been described in the literature of many different types. Dereniak et al., ("Snapshot dual-band visible hyperspectral imaging spectrometer", Optical Engineering Vol. 46(1), 2007) and Kudenov et al., ("Review of snapshot spectral imaging technologies", Optical Engineering 52(9), 090901 (September 2013)), discuss the use of Optical Computed Tomography (OCT) techniques to remove the use of moving parts in spectral imaging at the expense of spatial and spectral resolutions. Other snapshot methods described in Kudenov et al., have been developed. Such snapshot methods still provide a spectral image with intermediate resolution in both wavelength and space parameters, but the optical fabrication of the required exotic components is cumbersome and expensive (such as reformatting coherent fiber bundles, lenslet arrays, and multiple mirror facets).

SUMMARY OF THE INVENTION

The present invention is a reliable and low cost device for detecting, imaging and quantifying an airborne gas in a specific range of concentration and cloud size. The device uses no moving parts and has an optical system based on a bistatic electronically controlled notch absorber, absorbing in the same wavelength range as the gas to be detected. The device alternately images a field of view through a bistatic absorber in the notch and out-of notch wavelength ranges, respectively.

According to an embodiment of the teachings of the present invention there is provided, a device for imaging radiation from a scene, the radiation including at least a first and second wavelength band, the second wavelength band included in the first wavelength band, the device comprising: (a) a detector of the radiation from the scene sensitive to radiation in the first wavelength band; (b) an image forming optical component for forming an image of the scene on the detector; (c) a filtering arrangement including first and second independently controllable pluralities of radiation absorbing molecules in the second wavelength band, the filtering arrangement configured to be electronically switched between: (i) a first state, in which all of the radiation in the first wavelength band is transmitted to the detector, and (ii) a second state, in which the radiation in the second wavelength band is at least partially absorbed by each of the first and second pluralities of radiation absorbing molecules, and (d) a control unit electrically coupled to the filtering arrangement and the detector for synchronizing the switching of the filtering arrangement with the image forming on the detector, such that, each pixel of the formed image includes: (i) a first signal including information associated with the scene radiation in the first wavelength band, and (ii) a second signal including information associated with the scene radiation in the first wavelength band and excluding information associated with the scene radiation absorbed by the filtering arrangement in the second wavelength band.

Optionally, when the filtering arrangement is in the first state, the first plurality of radiation absorbing molecules are arranged in a first orientation substantially parallel to a direction of propagation of the radiation from the scene to the detector.

Optionally, when the filtering arrangement is in the second state, the first plurality of radiation absorbing molecules are arranged in a second orientation substantially perpendicular to a direction of propagation of the radiation from the scene to the detector.

Optionally, when the filtering arrangement is in the first state, the second plurality of radiation absorbing molecules is arranged substantially parallel to the first plurality of radiation absorbing molecules.

Optionally, when the filtering arrangement is in the second state, the second plurality of radiation absorbing molecules is arranged substantially perpendicular to the first plurality of radiation absorbing molecules.

Optionally, the first and second pluralities of radiation absorbing molecules are arranged in series such that the second plurality of radiation absorbing molecules is interposed between the first plurality of radiation absorbing molecules and the detector.

Optionally, the first plurality of radiation absorbing molecules are positioned within a first cell, and the second plurality of radiation absorbing molecules are positioned within a second cell.

Optionally, the radiation from the scene is unpolarized.

Optionally, when the filtering arrangement is in the second state, the radiation in the first wavelength band is polarized by the first plurality of radiation absorbing molecules.

Optionally, the first plurality of radiation absorbing molecules is configured to polarize the radiation incident from the scene.

Optionally, the second plurality of radiation absorbing molecules is configured to polarize the radiation incident from the first plurality of radiation absorbing molecules.

Optionally, the image forming optical component has an optical f-number less than approximately 1.5.

Optionally, the filtering arrangement is interposed between the scene and the image forming optical component.

Optionally, the filtering arrangement is interposed between the detector and the image forming optical component.

Optionally, each of the first and second pluralities of radiation absorbing molecules includes liquid crystal molecules.

Optionally, the radiation in the first wavelength band includes radiation in the range of 3.2-3.5 micrometers in wavelength.

Optionally, the first and second signals provide quantitative information about the scene, the quantitative information produced by an analytical technique.

Optionally, the scene is a gas cloud.

Optionally, the gas cloud is a hydrocarbon gas cloud.

BRIEF DESCRIPTION OF THE DRAWINGS

The invention is herein described, by way of example only, with reference to the accompanying drawings, wherein:

FIG. 3A is plot of the transmittance of a filter according to an embodiment of the invention;

FIG. 3B is a plot of the transmittance of a gas cloud imaged by the device of FIG. 2;

FIG. 4 is a plot of detected radiation for different filter transmittance values as a function of gas cloud absorption;

FIG. 8A is an illustration of two cells of radiation absorbing molecules in a second state in which incident light is at least partially absorbed in the absorption wavelength range of the radiation absorbing molecules;

FIG. 8B is an illustration of two cells of radiation absorbing molecules in a first state in which incident light is completely transmitted in the detector wavelength range of sensitivity, including the absorption wavelength range of the radiation absorbing molecules.

DESCRIPTION OF THE PREFERRED EMBODIMENTS

Figure 1:
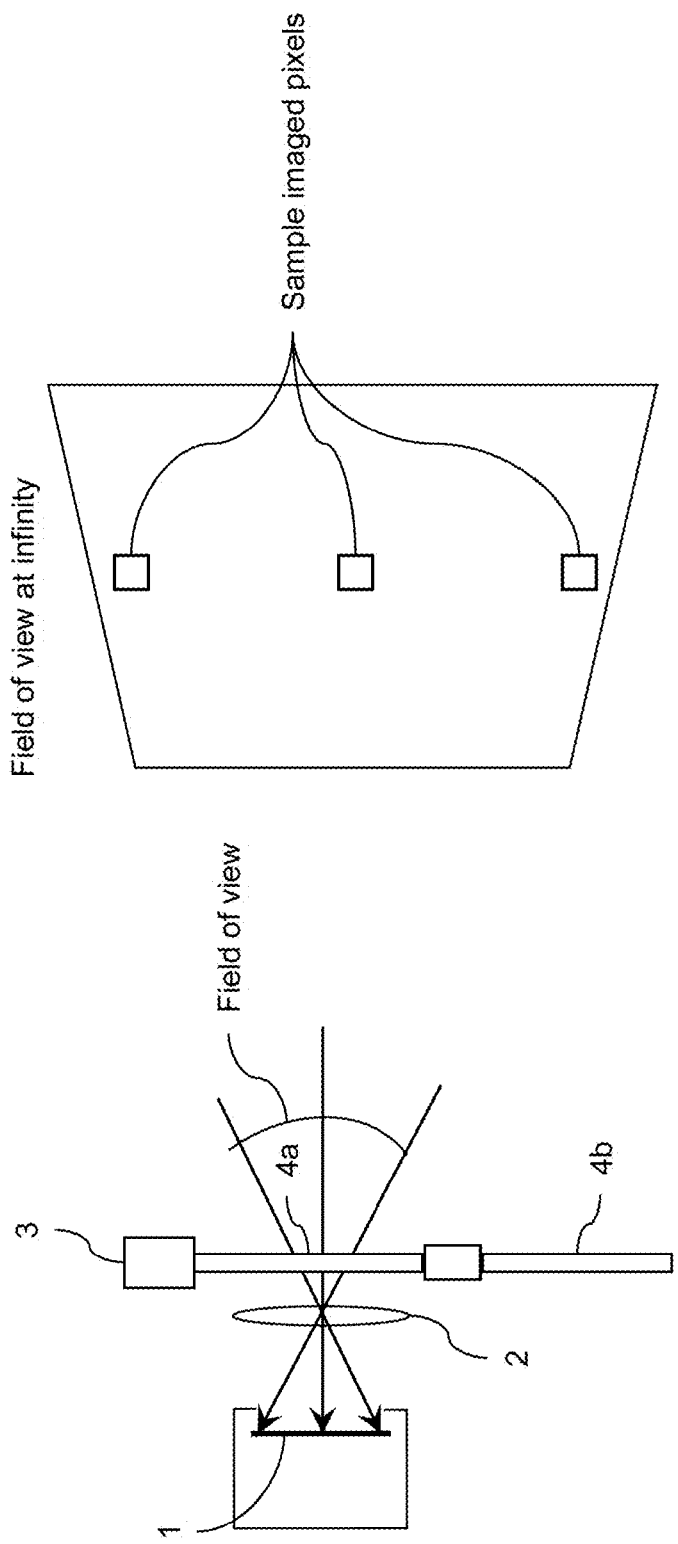
FIG. 1 is a schematic side view illustrating a prior art device for detecting and imaging radiation from a gas cloud.

The principles and operation of the device according to the present invention may be better understood with reference to the drawings and the accompanying description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways. Initially, throughout this document, references are made to directions such as, for example, right, left, and the like. These directional references are exemplary only to illustrate the invention and embodiments thereof.

The present disclosure is of a device for detecting and imaging a specific gas in the air in a specific range of concentration and cloud size that may be among the least expensive to build and most reliable, by avoiding the use of moving parts, and for measuring the path concentration of the gas in each pixel of the image. This is made possible, as will be explained in the following sections, by a compromise on the number of wavelength ranges combinations used, coming down to only two, by the use of an infrared sensitive camera (preferably uncooled or thermoelectrically cooled such as a PbSe camera sensitive to the 1 to 5.5 micron range, or microbolometer in the to 14 micron range), and by an optical system based on a bistatic electronically controlled notch absorber, absorbing in the same wavelength range as the gas to be detected. Other cooled cameras may be used at higher expense. The device alternately images a field of view through a bistatic absorber in the notch and out-of notch wavelength ranges respectively. A mathematical relation between the two signals (in and out-of-notch) at each image pixel is then used to calculate the path concentration of the gas making out the hazardous cloud present in the corresponding region of space, as will be explained in Section 1 below.

1. Gas Detection And Imaging Using Two-Wavelength Passive Infrared Radiometry:

It has been well known for many years that it is possible to detect the presence of a gas in the air and measure the corresponding path concentration distribution by measuring the infrared self-emission of the background of the gas cloud in two different wavelengths, one which is absorbed by the gas and one which is not, provided that the background and gas are not at the same temperature. The radiance difference R reaching the measuring instrument between the two wavelengths $w_0$ (not absorbed) and $w_G$ (absorbed by the gas), can be expressed in terms of the background radiance B, the gas temperature $T_G$ (usually equal to the air temperature, and we assume that it is known by measurement) and the gas transmittance $t_G$ at the absorbed wavelength. The gas transmittance $t_G$ is in turn dependent on the molecular absorption coefficient of the gas in question multiplied by the cloud thickness and gas molecular concentration at the pixel in question (referred to as the path concentration). Therefore, if the gas in question is known, the gas path concentration can be estimated. The following will clarify the quantitative method of the present disclosure by showing that $t_G$ can be measured with the present device, which in turn allows for the gas path concentration to be estimated:

$$R = B - B^* t_G - (1-t_G)^* Pl(T_G, w_G) = (1-t_G)^* \{B - Pl(T_G, w_G)\} \quad (1)$$

where $Pl(T_G, W_G)$ is the Planck function at temperature $T_G$ and wavelength $w_G$. Two simplifications are used in equation (1) which are not important for the sake of this explanation because the associated phenomena can both be calibrated out in the more general case: i) atmospheric transmittance is assumed to be 1, and ii) background radiance in and out of the gas absorption band are equal.

It is obvious from equation (1) that in the case that B is equal to $Pl(T_G, W_G)$, the radiance difference R is equal to zero, irrespective of the value of $t_G$, and in this case no information can be inferred on the quantity $t_G$. However, if B is different than $Pl(T_G, W_G)$, then equation (1) can be solved for $t_G$ as follows:

$$t_G = 1 - \frac{R}{B - Pl(T_G, w_G)} \quad (2)$$

All parameters on the right hand side of equation (2) are known: B is known because it is measured in the non-absorbing wavelength $w_0$, Pl is known because $T_G$ is measured and $w_G$ is known, and R is measured. Therefore $t_G$ is known from equation (2). If the molecular absorption coefficient, $A_G$, of the specific gas being monitored is known from the literature at $w_G$, then $t_G$ gives a measure of the product of average gas volume concentration in the cloud, multiplied by the thickness of the cloud itself, or the so called concentration times length (or path concentration) value of the cloud. In fact, by the Lambert-Beer law as follows:

$$t_G = e^{-nA_G l} \quad (3)$$

where l is the path length or thickness of the cloud and n is the average volume concentration of the gas being measured in the cloud, both corresponding to a specific pixel being examined. From equation (3), nl can be expressed as:

$$nl = \frac{1}{A_G} \ln\left(\frac{1}{t_G}\right) \quad (4)$$

If l is known then the average concentration n can be estimated by:

$$n = \frac{1}{lA_G} \ln\left(\frac{1}{t_G}\right) \quad (5)$$

Note that the estimated average concentration n expressed in equation (5) assumes absorption from single molecules, negligible attenuation effects from scattering, reflections, and multiple absorption in the gas cloud. In general, l is not known and $A_G$ is known, so this method readily provides nl according to equation (4), once $t_G$ is measured according to equation (2).

The purpose of the present invention is to give a solution to the problem of detecting and imaging the concentration times path length distribution of an infrared wavelength absorbing gas cloud (or other similar material with an absorbing wavelength) with the minimum use of moving parts and at the same time retaining the best sensitivity possible.

FIG. 1 depicts an example of a prior art solution. In such a solution, an objective lens 2 is positioned in front of a detector array 1 and a two-position filter holder or wheel 3 containing two filters (4a,4b), either in front of the objective lens 2 or between the objective lens 2 and the detector array 1. In this way, by recording successive images of the field of view (FOV) of the instrument at the two wavelength bands the needed information is gathered to detect the gas, if present, and in this case, calculate the concentration times path value of the gas in question for every pixel of the scene, as explained above. From this information the image of the cloud is built pixel by pixel and either displayed in an enhanced color, or otherwise used, e.g. to issue an alarm if this value becomes higher than a minimum safety value in some predefined spatial criteria. In the example shown in FIG. 1, the filter holder 3 slides in front of the objective lens 2 in a linear motion. Other configurations using rotating wheels, grating, etc. to filter the different wavelengths can be used, but they all use moving parts. The filters are before the objective lens. Only the principal rays of the central, top and bottom pixels of the FOV are shown. The filters can be alternately placed between the lens and the detector or between lenses in a multiple lens system design.

It should be noted that the configuration of FIG. 1 can be preferably designed with a large numerical aperture of the objective lens 2 to exploit the best possible detector sensitivity (or low f-number, which is in general kept as close to 1 as possible, especially when using cooled infrared detector arrays). A different configuration, using a dichroic beamsplitter to split the incoming beam into two beams to be filtered separately in the two wavelengths and two separate detectors can be used, but would be more expensive because of the additional detector cost. A further similar configuration using, besides the dichroic filter, an additional beam combiner and chopper may be used to limit the design to the single array detector, but in this case the chopper, needed to switch between the two wavelengths in synchronization with the detector frame capture rate, is a low reliability moving part. These last two configurations require more complicated optics to avoid decreasing the numerical aperture of the focusing optics at the detector and degrade the system sensitivity.

Figure 2:
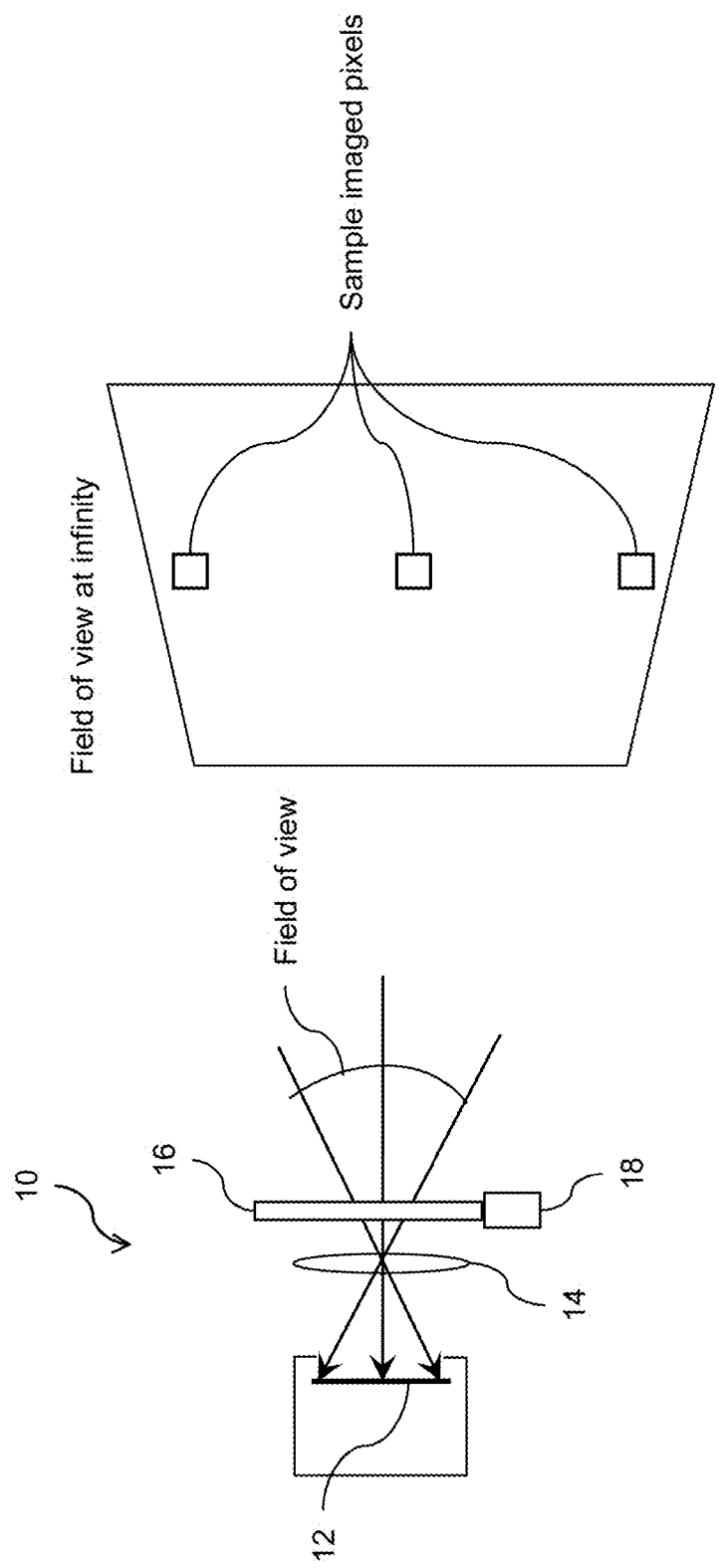
FIG. 2 is a schematic side view illustrating a device for detecting and imaging radiation from a scene according to an embodiment of the invention.

2. Bistatic Liquid Crystal Solution:

Refer now to FIG. 2, a device 10 of an embodiment of the present invention. The device 10 enables imaging the same region of space or field of view (FOV) alternately through two electronically controlled filtering states, using a single detector array camera 12 and optical system without mechanical movement of any optical component (the shutter is still needed to carry out NonUniformity Corrections, including environmental drifts, fixed pattern and readout noise), while preserving the high optical throughput of the conventional configurations previously described in the Section 1. This is accomplished by a combination of an imaging optics 14 (referred to interchangeably as focusing optics, image forming optics, and objective lens) with f-number close to 1 (high numerical aperture) and a bistatic liquid crystal (LC) based notch filter 16 (referred to interchangeably as LC filter, LC notch, LC notch filter, bistatic LC filter, bistatic LC notch filter) having a spectral behavior optimized to the gas absorption spectrum in question. The LC filter configurations pair are, as explained in the example below, i) a high filter transmittance spectral region, and ii) a notch filter absorbing in a region around a wavelength absorbed by the gas, this wavelength being within the high transmittance wavelength region. These two configurations are alternately switched electronically by a controller 18 in synchronization with the camera frames recording. In this way the device 10 records two signals for each pixel, one through the high transmittance and one through the notch configuration. In Section 3 we show how to calculate $t_G$ of equation (1) from these two pixel signals.

The controller 18 can be implemented as any number of computer processors including, but not limited to, a microprocessor, an ASIC, a DSP, a state machine, and a microcontroller. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions.

Once $t_G$ is known in every pixel, equation (4) yields the information of concentration times path length of the gas cloud at every point in the image. From this information one can build the image in false color or in different intensity levels of the color, according to the nl value of the gas being monitored at every pixel. Capturing alternating information in these two configurations on the same detector 12 according to the present invention also allows the monitoring of faster phenomena than in a conventional configuration, because the electronic switching between the "off" (high transmittance) and "on" (notch transmittance) configurations of the filter can be done at high frequencies of several kHz. This is due to the fast LC molecules response to the suitably applied high frequency alternating voltage. With the proper digital analysis, the final gas cloud image can be shown superimposed on a conventional visible image of the same field of view, obtained by a usual visible CCD camera. This helps the operator locate the cloud with respect to other objects in the field.

With continued reference to FIG. 2, the edge and central rays of the FOV are depicted passing through the two bistatic filter 16 and focusing optics 14, and forming the scene image on the detector plane. The view in FIG. 2 is a cross section from the side of the device 10. The moving filter holder or wheel 3 of FIG. 1 is replaced by the electronically controlled bistatic LC filter system (the bistatic LC filter 16 and the controller 18), including a high transmittance configuration in a wavelength range, alternating with a notch absorbing filter configuration in a sub-range corresponding to the gas absorption wavelength.

3. Gas Path Concentration Measurement:

As explained in Section 1 with reference to equation (4), if the absorption coefficient of the gas molecules being monitored is known from the literature and the cloud transmittance is measured, then the cloud path concentration can be at least approximately calculated. In this section it is shown how the signals through a bistatic notch filter can be used to calculate the transmittance through the gas cloud.

In FIG. 3A the transmittances of the bistatic LC filter 16 in the off and on configurations are shown. The dotted line is the "off" configuration (i.e. no notch region). In the "off" configuration, there is 100% transmittance in the range between $\lambda_1$ and $\lambda_2$ and 0% transmittance outside of that range). In the "on" configuration, the transmittance is a notch centered at and width w. The transmittance in the notch region is z.

In FIG. 3B, the gas cloud transmittance in a pixel of path concentration nl is shown. The absorption wavelength range is centered in the same wavelength $\lambda_0$ as the LC notch and has the same width w. The transmittance in the absorption range is x and 100% otherwise.

The detector array 12 is assumed to be sensitive only in the wavelength region between $\lambda_1$ and $\lambda_2$. Now assume that the spectral radiance of the cloud background is B and is a constant function of wavelength. Then, in view of FIGS. 3A and 3B, the average radiance reaching the detector array 12 in the wavelength range between $\lambda_1$ and $\lambda_2$ can be expressed for four cases. Defining $D=\lambda_2-\lambda_1$ and $y=w/D$, where w is defined above, the four cases are defined as follows:

First case: gas present (G), notch on (N):

$$\frac{S_{G,N}}{D} = B\left(1 - \frac{w}{D}\right) + \frac{Bwxz}{D} = B(1-y) + Byxz \qquad (6)$$

Second case; gas present (G), notch off (O):

$$\frac{S_{G,O}}{D} = B\left(1 - \frac{w}{D}\right) + \frac{Bwx}{D} = B(1-y) + Byx \qquad (7)$$

Third case: gas absent (A), notch on (N):

$$\frac{S_{A,N}}{D} = B\left(1 - \frac{w}{D}\right) + \frac{Bwz}{D} = B(1-y) + Byz \quad (8)$$

Fourth case: gas absent (A), notch off (O):

$$\frac{S_{A,O}}{D} = \frac{ED}{D} = B \quad (9)$$

Equations (8) and (9) are special cases of equations (6) and (7) respectively for x=1. This should be apparent, as x=1 implies that the gas cloud is absent. In this case the right hand side of equation (6) is the same as in equation (8) and the right hand side of equation (7) becomes equation (9). Similarly, for a very, high concentration gas cloud, x=0, and equations (6) and (7) give the same result. This is because the total signal is B multiplied by the product of the two transmittance functions in FIGS. 3A and 3B. If the gas cloud absorbs all radiation within the notch range the signal is independent on whether the LC notch is in the on or off configuratio.

A ratio, F, of the difference between "on" and "off" and the "off" signal (or normalized signal contrast) can be calculated from equations (6) and (7). The ratio IF can be expressed as follows:

$$F = \frac{S_{G,O}/D - S_{G,N}/D}{S_{G,O}/D} = \frac{yx(1-z)}{1 - y(1-x)} \quad (10)$$

Equation (10) is the basic relation between the pixels' signals in the LC on and off positions and the quantity x, which is equal to $t_G$ of equation (3) above, in turn the parameter related to the path concentration of the gas cloud in question according to equation (4).

The ratio F of equation (10) can be plotted as function of the total gas cloud absorption ($\ln(1/x) = nlA_G$ of equation (4)) for different values of y and z. Example plots are shown in FIG. 4.

The plotted values of FIG. 4 are calculated for y=0.8. (y can change by definition between 0 and 1, but these two values are limiting values that have no physical meaning for our purpose). In fact, y=0 is not physical and for y=1, F does not depend on x. The exact values of y and z should be selected according to the design of the device 10. In practice, the values of y and z are typically measured separately in the laboratory or known from the literature. Once y and z are known, the function F of equation 10 is plotted as a function of x for these values of y and z. $x=t_G$ is then determined by determining the value of $\ln(1/x)$ corresponding to the measured value of F for the particular pixel in question on the plotted graph. This can be done, since the plotted functions of F, as seen in FIG. 4, are monotonic, and therefore have one-to-one relationships. Alternatively, equation (10) can be inverted to express x as function of F, y and z. Again, once F is measured with the device 10 and y and z are known independently, $x=t_G$ (and therefore is also known.

It is noted that the above example refers to the case in which the background of the gas cloud is at higher temperature than the cloud itself, so that the gas appears as absorbing. However, the same arguments can be shown to hold in the opposite case of background being cooler than the gas cloud, when the gas appears as an emitter.

4. Liquid Crystal Implementation

In this section, implementation of the bistatic notch LC filter 16, in order to provide the type of signals as described above without moving parts, is discussed. This section also addresses the integration of the bistatic notch LC filter 16 in the device 10, in order to detect and image a gas cloud. The implementation and integration discussion is applied, as a non-limiting example, to a group of hydrocarbons that all have an absorption around the same wavelength range, between 3.2 and 3.5 microns, and to a particular detector type that is sensitive in that range. As should be apparent to one of ordinary skill in the art, many other combinations of materials to be detected, LC filters materials, and different detectors may be used according to the teachings of the present embodiments described herein.

Figure 5:
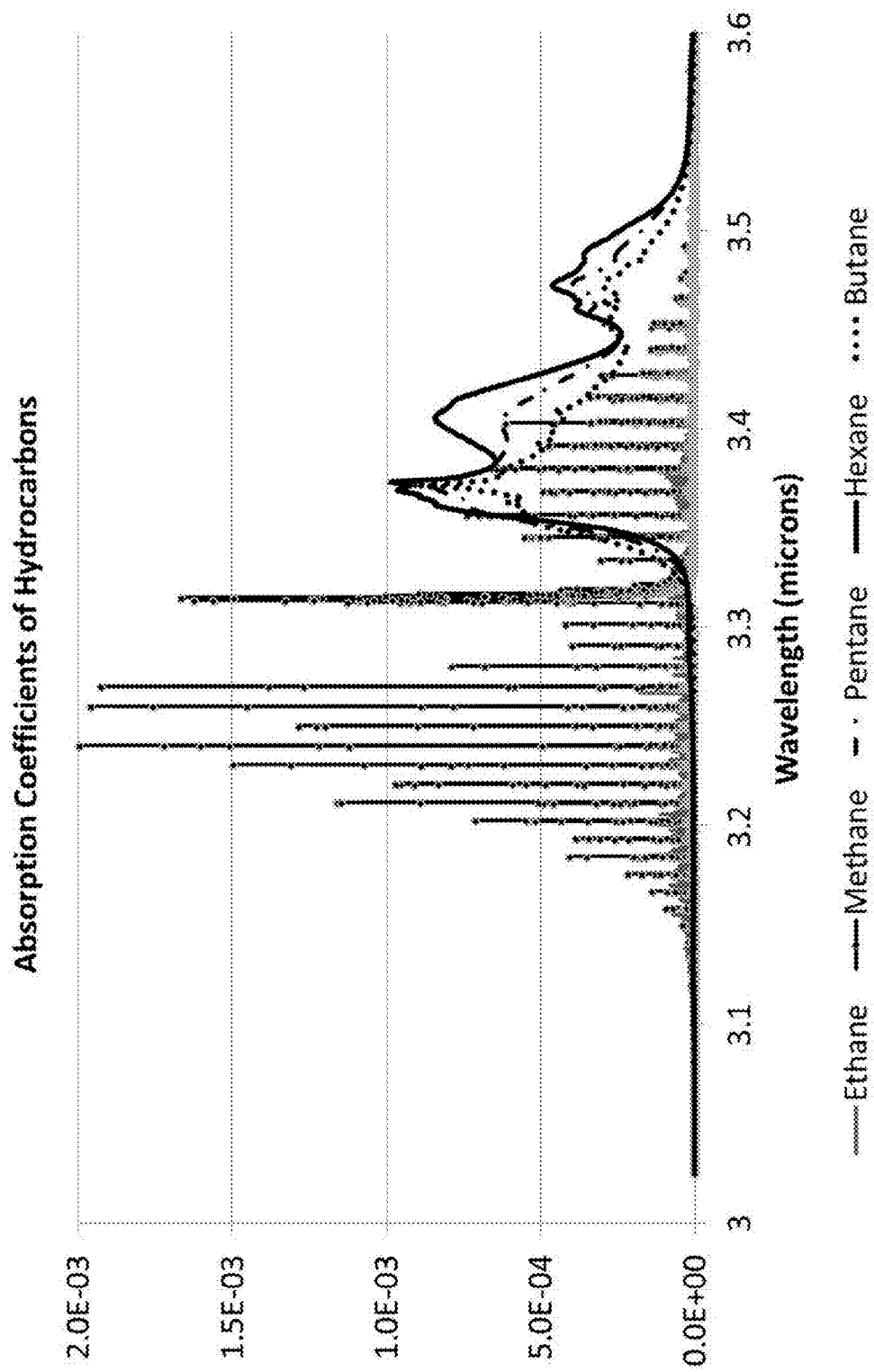
FIG. 5 is a plot of the absorption characteristics for a group of hydrocarbon gases.
Figure 6:
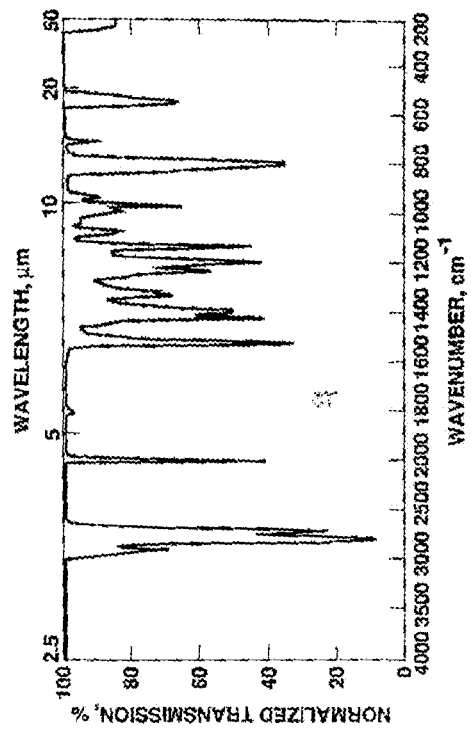
FIG. 6 is a plot of the transmission characteristics of a liquid crystal.

The absorption characteristics for the non-limiting example group of hydrocarbons are shown in FIG. 5. In the particular wavelength range of hydrocarbons pertinent to the present non-limiting example, there exist liquid crystals, such as, for example, E-7 and BDH-E7. Such liquid crystals present absorption in this wavelength range. The transmission characteristics of such example liquid crystals are shown in FIG. 6 which is an excerpt from the Handbook of Optics, McGraw-Hill Inc., Sponsored by the Optical Society of America, Volume II, page 14.6, 1995.

As described, for example, by C. L. Mulder et al., in the publication Dye alignment in luminescent solar concentrators: I. Vertical alignment for improved waveguide coupling, Optics Express Vol. 18, No. S1, p. A79, 2010, there are at least two ways to obtain the same desired effect. One is that the LC itself preferentially absorbs infrared radiation polarized along the long molecular direction and does not appreciably absorb radiation polarized perpendicular to that direction, including when the molecule is aligned parallel to the incoming infrared light propagation direction. The second way is to have a long absorbing molecule embedded in the LC matrix, such that its polarization properties are controlled in a similar way by the LC molecules alignment. In both cases a cell containing the LC itself or the molecular mixture mentioned here, can be electronically induced to absorb radiation anisotropically, as shown in FIG. 7A.

Figure 7B:
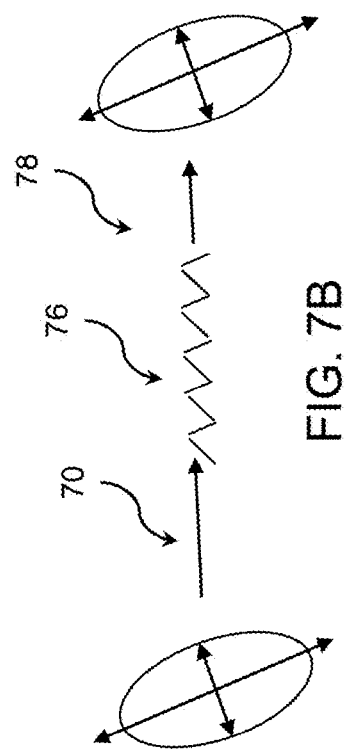
FIG. 7B is an illustration of radiation absorbing molecules in an unpolarizing state.
Figure 7A:
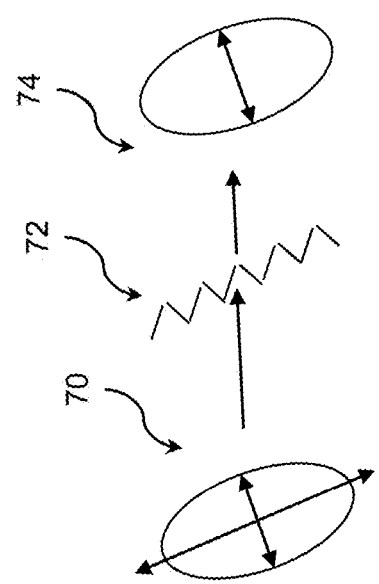
FIG. 7A is an illustration of radiation absorbing molecules in a polarizing state.

In FIG. 7A, unpolarized light 70 is incident from the left on an LC 72 or absorbing long molecule oriented perpendicularly to the light propagation direction. The transmitted light at wavelengths within the gas and LC absorption wavelength region is polarized perpendicularly to the long axis of the molecule. Light outside this band is not absorbed and is unpolarized. As a result, in this example, molecules oriented perpendicularly to the light propagation direction have the following effect: they absorb the portion of light around the 3.5 microns range which is polarized parallel to their long molecular axis, while transmitting the same wavelength range polarized in a direction perpendicular to their long molecular axis (depicted as a transmitted polarized light beam 74 around the gas absorption wavelength); in addition, light outside the 3.5 micron wavelength range is completely transmitted.

Alternately, when these molecules are placed in a cell and the appropriate voltage is applied to it so that their long axis is aligned with the propagation direction of the incoming light, they do not absorb any light and in this situation all radiation is transmitted through the cell, as shown in FIG. 7B.

In FIG. 7B, the unpolarized light 70 is incident on an LC long molecule 76 whose long axis is oriented in the direction of the light propagation direction. As a result, all light is transmitted and is unpolarized (depicted as a transmitted unpolarized light beam 78). The configuration depicted in FIG. 7B is the "off" filter configuration of the LC filter 16.

Now consider, as in FIGS. 8A and 8B, a system composed of two equal LC cells in series (a first LC cell 80 and a second LC cell 82), where the molecules 81 in the first LC cell 80 and the molecules 83 in the second LC cell 82 are oriented with their long axis in two perpendicular directions with respect to each other and to the light propagation direction. An unpolarized light beam 84 incident from the left is completely (or partially) absorbed in the absorption wavelength range of the molecule and gas by the pair of cells (this is the "on" filter state of the LC filter 16 described in Section 3 above). This is due to the fact that the second LC cell 82 absorbs the residual polarized light 85 transmitted by the first LC cell 80 (functioning as cross polarizers with respect to this radiation). All light outside that range is transmitted. When the molecules of both cells are switched electronically (via the control unit 18) to be oriented parallel to the light propagation direction as in FIG. 8B, no light is absorbed (this is the "off" state of the LC filter 16 described in Section 3 above). Specifically, in FIG. 8B, the unpolarized light beam 84 is transmitted unpolarized (and shown as 85) after passing through the first LC cell 80, and likewise by LC cell 82. As a result, all light incident on the first LC cell 80 passes through the second LC cell 82 within the whole wide band region between $\lambda_1$ and $\lambda_2$ of FIG. 3A.

As should be apparent from the discussion above, the device 10 (as shown in FIG. 2) in which the filtering element 16 is a bistatic filter as described above in Section 4, provides images of the scene in which each pixel's radiation is known according to the four equations (6), (7), (8), and (9). Accordingly, a procedure as described in Section 3 can be followed to detect a gas cloud having the above described absorption properties, if present in the air, and map the path concentration of the gas cloud pixel by pixel.

It will be appreciated that the above descriptions are intended only to serve as examples, and that many other embodiments are possible within the scope of the present invention as defined in the appended claims.

What is claimed is:

1. A device for imaging a scene, the device comprising:
   (a) a detector;
   (b) an optical arrangement defining an optical path from the scene to said detector;
   (c) a switchable filter comprising at least one cell of liquid crystal material, said switchable filter being deployed in said optical path; and
   (d) a controller for selectively switching said switchable filter between a first state, in which molecules of liquid crystal within said liquid crystal material are aligned in a first orientation, and a second state in which said molecules of liquid crystal are not aligned with said first orientation, said first and second states differing in their spectral absorption properties,
   wherein said controller is configured to switch said switchable filter synchronously with sampling of pairs of images of the scene formed on said detector, said pairs of images comprising a first image formed with said switchable filter in said first state and a second image formed with said switchable filter in said second state, and wherein the device is configured to co-process a first pixel signal associated with said first image and a second pixel signal associated with said second image to derive a spectrally selective difference pixel signal.

2. The device of claim 1, wherein said first orientation is substantially parallel with said optical path.

3. The device of claim 1, wherein, in said second state, a majority of said molecules of liquid crystal are aligned substantially perpendicular to said first orientation.

4. The device of claim 1, wherein said switchable filter comprises two cells of liquid crystal material, and wherein, in said second state, a majority of said molecules of liquid crystal in a first of said cells are aligned in a second orientation substantially perpendicular to said first orientation, and wherein, in said second state, a majority of said molecules of liquid crystal in a second of said cells are aligned in a third orientation substantially perpendicular to both said first orientation and said second orientation.

5. A method comprising:
   (a) deploying in an optical path of an imaging device a switchable filter comprising at least one cell containing liquid crystal material;
   (b) forming a first image on a detector of the imaging device while the switchable filter assumes a first state in which molecules of liquid crystal within the cell are aligned in a first orientation; and
   (c) forming a second image on the detector of the imaging device while the switchable filter assumes a second state in which the molecules of liquid crystal are not aligned with the first orientation, said first and second states differing in their spectral absorption properties; and
   (d) co-processing a first pixel signal associated with said first image and a second pixel signal associated with said second image to derive a spectrally selective difference pixel signal.

* * * * *

UNITED STATES PATENT AND TRADEMARK OFFICE
CERTIFICATE OF CORRECTION

PATENT NO. : 9,880,094 B2
APPLICATION NO. : 15/442715
DATED : January 30, 2018
INVENTOR(S) : Karni Wolowelsky It is certified that error appears in the above-identified patent and that said Letters Patent is hereby corrected as shown below:

In the Claims

Claim 5, Column 12:
Line 38: remove "and"

Signed and Sealed this
Eighth Day of May, 2018

Andrei Iancu
*Director of the United States Patent and Trademark Office*